United States Patent [19]  [11] Patent Number: 4,936,833
Sams  [45] Date of Patent: Jun. 26, 1990

[54] CARTRIDGE-HOLDER ASSEMBLY FOR MEDICATION DISPENSING UNIT

[75] Inventor: Bernard Sams, London, England

[73] Assignee: Hypoguard (UK) Limited, Woodbridge, England

[21] Appl. No.: 237,147

[22] Filed: Aug. 26, 1988

Related U.S. Application Data

[63] Continuation-in-part of Ser. No. 205,198, Jun. 10, 1988, Pat. No. 4,865,591, which is a continuation-in-part of Ser. No. 81,241, Aug. 4, 1987, abandoned.

[51] Int. Cl.$^5$ .............................................. A61M 5/24
[52] U.S. Cl. .................... 604/232; 604/208; 604/209; 604/220; 222/391
[58] Field of Search .................. 604/68, 72, 208–210, 604/218, 220, 232, 234, 197; 222/325, 340, 391

[56] References Cited

U.S. PATENT DOCUMENTS

| | | | |
|---|---|---|---|
| 2,646,798 | 7/1953 | Brown | 604/232 X |
| 3,110,309 | 11/1963 | Higgins | 604/201 |
| 3,930,499 | 1/1976 | Rimbaud | 604/197 |
| 3,976,069 | 8/1976 | Ong | 604/232 X |
| 4,573,973 | 3/1986 | Mezi | 604/197 |
| 4,592,745 | 6/1986 | Rex | 604/211 |

FOREIGN PATENT DOCUMENTS

22140 10/1961 German Democratic Rep. .................................... 222/391

Primary Examiner—Martin P. Schwadron
Assistant Examiner—Allen J. Flanigan
Attorney, Agent, or Firm—Willian Brinks Olds Hofer Gilson & Lione

[57] ABSTRACT

A cartridge assembly for a syringe-type medication dispensing unit includes a cartridge having a cartridge body with first and second ends. A pierceable membrane is mounted at the first end and a piston is mounted at the second end, with a volume of medication contained in the cartridge body between the membrane and the piston. A cartridge holder receives the cartridge and defines first and second ends. The first holder end defines a central opening and an external thread for mounting a double-ended needle. The second holder end defines an external thread for securing the holder to a medication dispensing unit and an actuating shoulder. The holder frictionally engages the cartridge to form an assembly which can be handled as a single modular unit with the cartridge held securely in the holder by frictional engagement.

23 Claims, 6 Drawing Sheets

CARTRIDGE-HOLDER ASSEMBLY FOR MEDICATION DISPENSING UNIT

CROSS REFERENCE TO RELATED APPLICATIONS

This application is a continuation-in-part of copending U.S. patent application Ser. No. 07/205,198, filed Jun. 10, 1988, now U.S. Pat. No. 4,865,591, which is in turn a continuation-in-part of U.S. patent application Ser. No. 07/081,241, filed Aug. 4, 1987, now abandoned. The entire text of these applications Ser. Nos. 07/205.198 and 07/081,241 is hereby incorporated by reference.

BACKGROUND OF THE INVENTION

The present invention relates to a cartridgeholder assembly for a measured dose medication dispensing device.

Patients suffering from diabetes often have to inject themselves with frequent doses of insulin and this can be done using a conventional syringe. However, such patients often also suffer from side effects of their illness and are not capable of accurately controlling the operation of such a syringe. It is therefore desirable that they should be provided with means for automatically administering an accurately controlled dosage. The dosage required by different patients can vary over quite wide ranges, from for example 2 units of insulin per dose to 30 or more units, and it is necessary to ensure that any device is capable of selecting a range of dosages simply and accurately.

Dispensing devices such as that shown in Rex U.S. Pat. No. 4,592,745 utilize a cartridge having a pierceable membrane at one end and a movable piston at the other, with a volume of a medication such as an insulin solution contained therebetween. The cartridge is mounted in a dispensing device which includes a plunger, a one-way mechanism that permits the plunger only to advance, and a mechanism for advancing the plunger to dispense medication.

The device disclosed in the Rex patent utilizes the rear rim of the cartridge to actuate the one-way mechanism: when the cartridge is removed the one-way mechanism releases, allowing the plunger to retract, but when the dispensing device is assembled with the cartridge in place the rear rim of the cartridge causes the one-way mechanism to engage the plunger. The cartridge is received loosely in a section of the device, and the one-way mechanism engaging apparatus resiliently holds the cartridge in position.

The dispensing device of the Rex patent has been proven effective and reliable in use. Nonetheless, it suffers from certain disadvantages related to the fact that the walls of the cartridge are formed of glass and in commercially practical cartridges it is difficult to control the overall length of the cartridge accurately. Resulting variations in the length of the cartridge cause the one-way mechanism to be engaged at a variable position as the cartridge enclosing section is screwed into place in the dispensing unit. If the cartridge is unusually long, the one-way mechanism will be engaged well before the cartridge enclosing section reaches its final position, and the plunger will then pressurize the contents of the cartridge as the section is screwed home. Such pressurization will produce a squirt of medication when the needle pierces the membrane. Some users may object to this unintended release of medication.

The variable length of the cartridge also imposes design constraints on the Rex dispensing device. As mentioned above, the cartridge fits loosely within the cartridge receiving section, and the cartridge is held in position by forces applied to the rear rim of the cartridge by the engaging apparatus for the one-way mechanism discussed above. This engaging apparatus must provide resilient support to the rim over the full range of cartridge lengths. Otherwise, the cartridge may be subjected to excessive axial forces, or it may alternately be left free to move axially in the dispensing device. The resilient mounting of the engaging apparatus in no way overcomes the problems discussed above related to unintended pressurization of the cartridge.

The present invention is directed to an improved cartridge-holder assembly that overcomes these prior art problems.

SUMMARY OF THE INVENTION

According to this invention, a cartridgeholder assembly is provided for a syringe-type medication dispensing unit. The cartridge comprises a cartridge body having first and second ends, a pierceable membrane mounted at the first end, and a piston mounted at the second end, with a volume of medication contained in the cartridge body between the membrane and the piston. The holder defines a first holder end which defines a central opening and means for mounting a double ended needle. The second holder end defines means for securing the holder to a medication dispensing unit and an actuating shoulder. The holder defines a central cavity shaped to receive and frictionally engage the cartridge to form an assembly that can be handled as a single, modular unit with the cartridge held frictionally in the holder.

This arrangement overcomes the prior art problems discussed above. The holder can easily be manufactured to high precision, and the actuating shoulder can therefore be accurately positioned to actuate the one-way mechanism just as the holder reaches its fully assembled position on the dispensing device. This substantially eliminates the problem of unintended pressurization of the cartridge before the needle is inserted into the membrane. Secondly, the releasable engagement between the cartridge and the holder allows the cartridge to be held in place without engagement of the rim. This relaxes design constraints on the engaging apparatus for the one-way mechanism.

As yet another advantage, the modular assembly of the holder and cartridge can be handled and assembled onto the dispensing device as a unit. This simplifies assembly by the patient.

The housing is preferably formed from a clear plastic material, and a user can therefore readily observe the movement of the piston within the cartridge and can assess the amount of medication in the cartridge. The housing also provides a measure of protection to the cartridge, both physical and against pathogenic organisms and other possible contamination.

The needle end of the cartridge can project through a terminal aperture in the housing or that end of the housing can be closed and can carry a needle or other outlet integrally therewith which projects axially inwardly into the housing to penetrate the membrane at the end of the cartridge.

The cartridge houses the piston which is to be moved by the plunger of the dispensing device. This piston can be of conventional design and will usually form part of the cartridge as commercially available. The plunger acts on the piston and the piston can carry a socket or other recess to receive and locate the head of the plunger. In some cases, the plunger can be affixed to the piston and will form part of the cartridge as supplied, in which case the plunger will extend into the device when the cartridge is mounted on the device. However, it is preferred that the plunger form part of the device rather than of the cartridge and, for convenience the invention will hereinafter be described with respect to this configuration.

The invention itself, together with further objects and attendant advantages, will best be understood by reference to the following detailed description. taken in conjunction with the accompanying drawings

DETAILED DESCRIPTION OF THE PRESENTLY PREFERRED EMBODIMENTS

FIGS. 1-10 show various views of the preferred embodiment of the cartridge-holder assembly of this invention, and FIGS. 11-15 provide further details relating to a preferred dispensing unit suitable for use with the cartridge-holder assembly of FIGS. 1-10.

Figure 1:
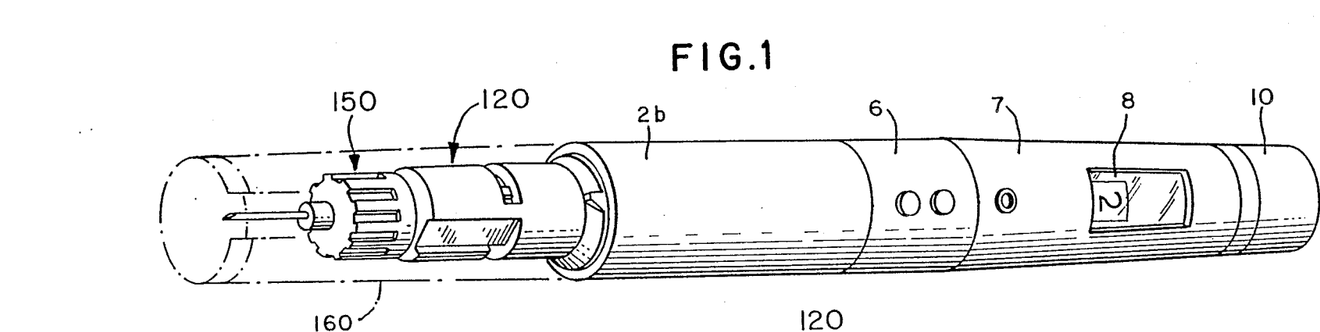
FIG. 1 is a perspective view of a syringe-type medication dispensing unit which includes a preferred embodiment of the cartridge-holder assembly of this invention.
Figure 2:
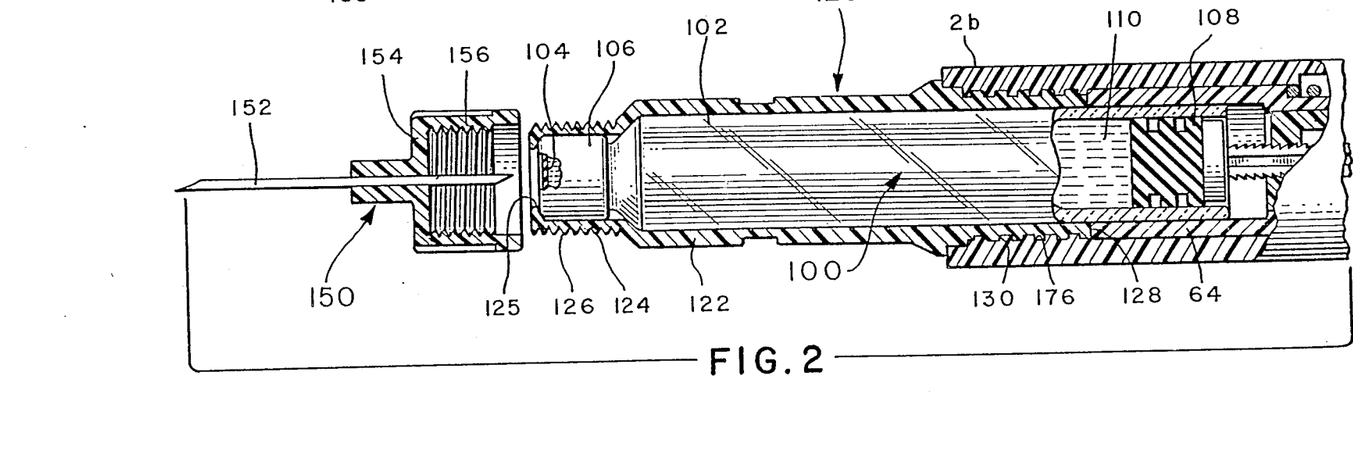
FIG. 2 is a partial view of portions of the unit of FIG. 1 in partial section.
Figures 3, 4:
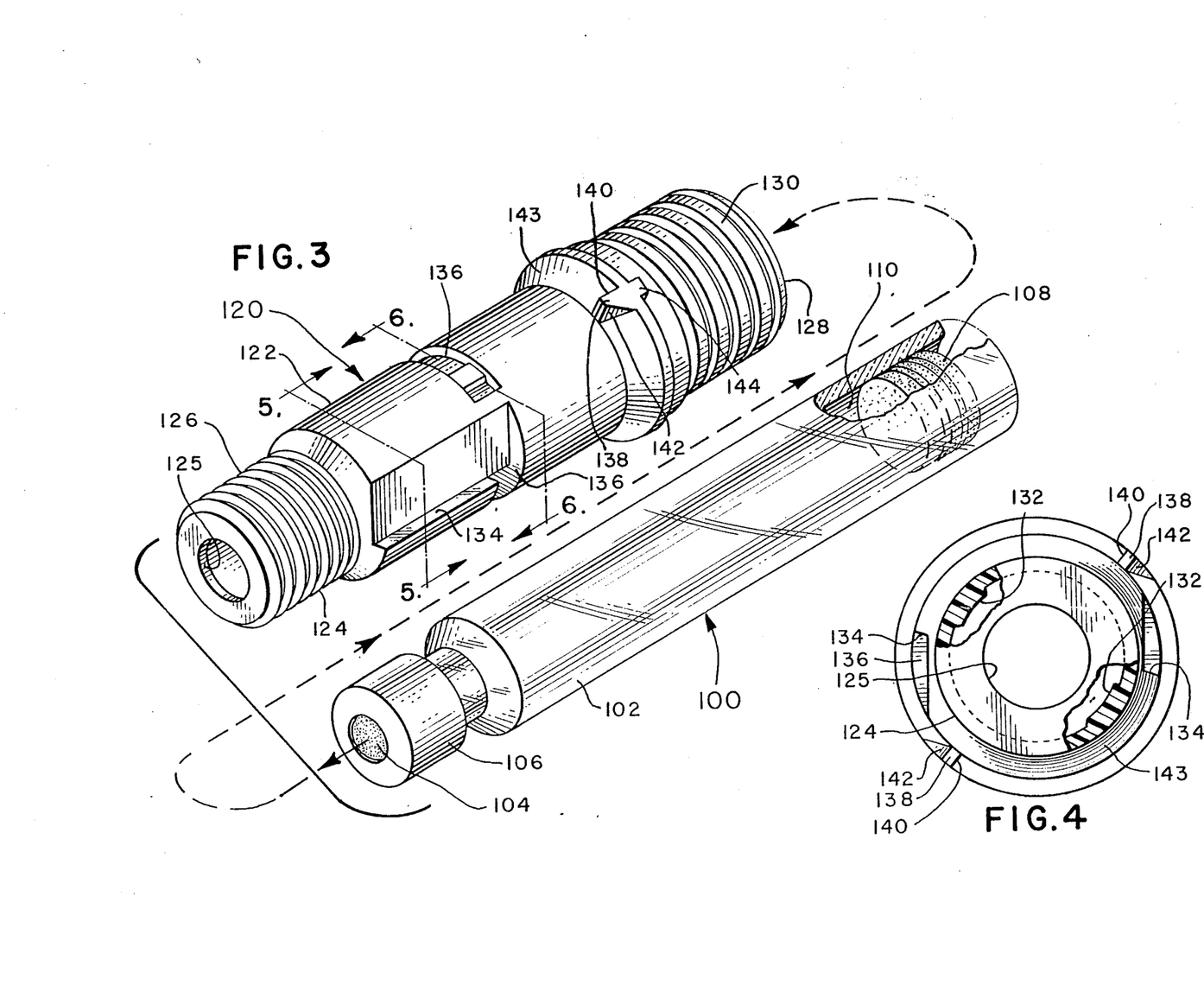
FIG. 3 is an exploded perspective view of the cartridge-holder assembly of FIG. 1.
FIG. 4 is a front view in partial cutaway of the holder of FIG. 3.
Figures 5, 6:
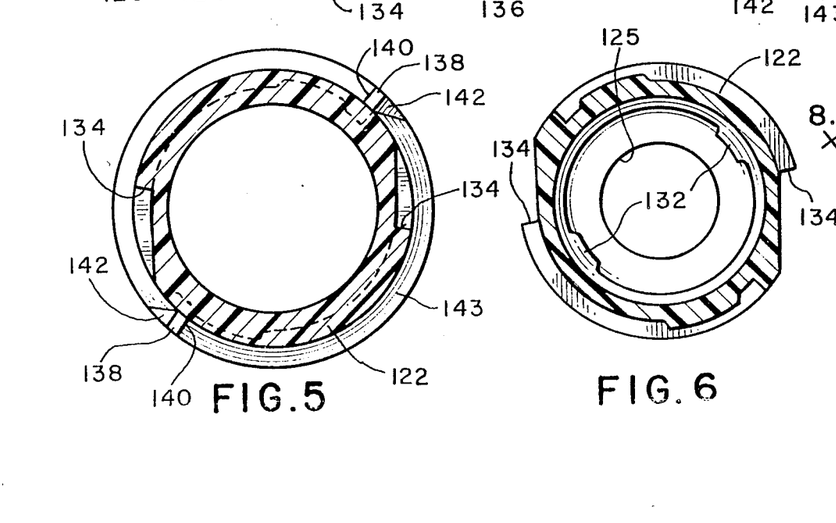
FIG. 5 is a cross sectional view taken along line 5—5 of FIG. 3.
FIG. 6 is a cross sectional view taken along line 6—6 of FIG. 3.
Figure 7:
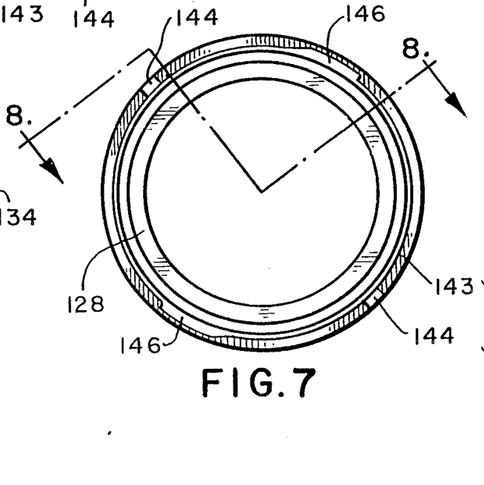
FIG. 7 is a rear view of the holder of FIG. 3.

Turning now to FIGS. 1-10, the preferred embodiment of the assembly of this invention comprises a cartridge 100 and a cartridge holder 120. FIG. 1 shows the holder 120 mounted to a dispensing device, and FIG. 2 shows the cartridge 100 mounted within the holder 120. As best shown in FIGS. 2 and 3, the cartridge 100 includes a generally cylindrical body 102 which is closed at one end by a pierceable membrane 104 and is sealed at the other end by a movable piston 108. A medication such as an insulin solution 110 is contained within the body 102 between the membrane 104 and the piston 108. In the conventional manner, a collar 106 of metal surrounds the membrane 104 and secures the membrane 104 to the body 102 in a fluid-tight manner.

The cartridge 100 can be quite similar to conventional glass cartridges. Of course, the dimensions of the cartridge should be chosen to match the dispensing device. Preferably, the body 102 is glass coated with silicone to reduce friction with the piston. The piston 108 is preferably about two-thirds the axial length of conventional pistons, also to reduce friction.

Figure 8:
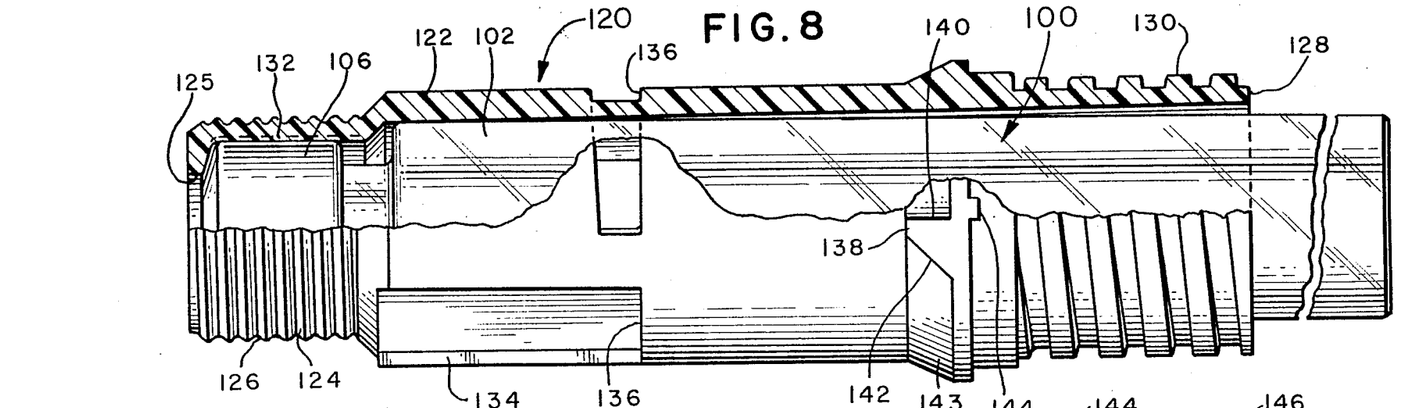
FIG. 8 is a longitudinal sectional view taken along line 8—8 of FIG. 7 in partial elevation.

As best shown in FIGS. 2 and 8, the cartridge holder 120 comprises a tubular element 122 which defines a narrowed neck 124 which terminates in a central opening 125. External threads 126 are formed around the exterior of the neck 124. The opposite end of the cartridge holder 120 defines an annular actuating shoulder 128 positioned adjacent to a second set of external threads 130. The tubular element 122 is sized to receive the cartridge 100 and defines in this embodiment two axially oriented raised lands 132 which are positioned to frictionally engage the collar 106 of the cartridge 100.

The exterior of the tubular element 122 defines a number of features which cooperate with other components of the dispensing device described below. In particular, the tubular element 122 defines a pair of axial grooves 134 which communicate with respective circumferential grooves 136 to form L-shaped grooves that form part of a bayonet mount as described below. The tubular element 122 also defines a pair of stop members 138 which cooperate with a cap as described below. Each of the stop members 138 defines a transverse face 140 and an opposed sloping face 142. The tubular element 122 also defines an annular flange 143 which in turn defines two rearwardly extending stop members 144. A pair of ramps 146 are defined on the exterior of the tubular member 122 near the external threads 130.

Preferably, the cartridge holder 120 is formed of a transparent plastic material such as polycarbonate. This construction allows a user to see the cartridge 100 within the cartridge holder 120 to check the correct insulin and to gauge the amount of medication 110 left in the cartridge 100.

The minimum diameter of the inside of the tubular element 122 is greater than the maximum diameter of the cartridge 100. For this reason, the tubular element 122 receives the cartridge 100 in an easy sliding fit such that the weight of the cartridge 100 will move the cartridge 100 in the tube 122 until the collar 106 contacts the raised lands 132. A slight additional force will push the cartridge 100 to the fully seated position shown in FIG. 8. In this position friction between the lands 132 and the collar 106 will prevent the cartridge 100 from falling out of the holder 120. This arrangement facilitates assembly of the cartridge 100 into the holder 120, because no frictional retarding force is encountered until the cartridge 100 is almost in the fully assembled position. There is therefore, less chance that a user will fail to push the cartridge 100 fully into the holder 120. Furthermore because the cartridge 100 is engaged at the collar 106, it is the diameter of the collar 106 rather than the diameter of the tube 122 that determines the tightness of the friction fit. In many cases, the diameter of the collar 106 can be controlled more closely than the diameter of the glass tube 122, and in these cases this arrangement provides the further advantage of a more consistent fit.

Thus, the lands 132 frictionally engage the collar 106 to releaseably hold the cartridge 100 in the holder 120 and thereby to form a modular unit which can be handled and assembled as a single device. As apparent in FIGS. 2 and 8, the end of the cartridge 100 that mounts the piston 108 extends out of the cartridge holder 120 for a considerable distance. In this embodiment, that distance is greater than one-half inch. This allows the user to grasp the cartridge 100 when it is necessary to remove the cartridge 100 from the cartridge holder 120 for replacement.

As shown in FIG. 2, the external threads 126 are sized to mate with internal threads 156 defined by a needle assembly 150. This needle assembly 150 includes a double-ended hypodermic needle 152 which is mounted to a hub 154 that in turn defines the internal threads 156. By threading the needle assembly 150 onto the external threads 126 the needle 152 is passed through the central opening 125 and the membrane 104, into contact with the medication 110.

As shown in FIGS. 1 and 11-13 the dispensing device includes a removable cap 160 which, when mounted in position, surrounds and protects the needle assembly 150 (if mounted), the cartridge holder 120, and the cartridge 100. This cap 160 defines a pair of internal lugs 162 sized to fit within the grooves 134, 136 to form a bayonet mount in order to hold the cap 160 securely in position on the cartridge holder 120. In addition, the cap 160 defines a pair of protruding elements 164 positioned to interact with the stop members 138. When the cap 160 is rotated in a first locking direction, the protruding elements 164 engage the transverse faces 140, thereby defining a stop position. This allows the cap 160 to be used as a tool to apply torque to screw the cartridge holder 120 into place on the dispensing device without overtightening the bayonet mount. When the cap 160 is rotated in a second unlocking direction, the protruding elements engage the sloping faces 140 to shift the cap 160 axially. The cap 160 can if desired define a clip 166 to retain the dispensing device in a pocket of the user.

Figures 9, 10, 11, 12, 13:
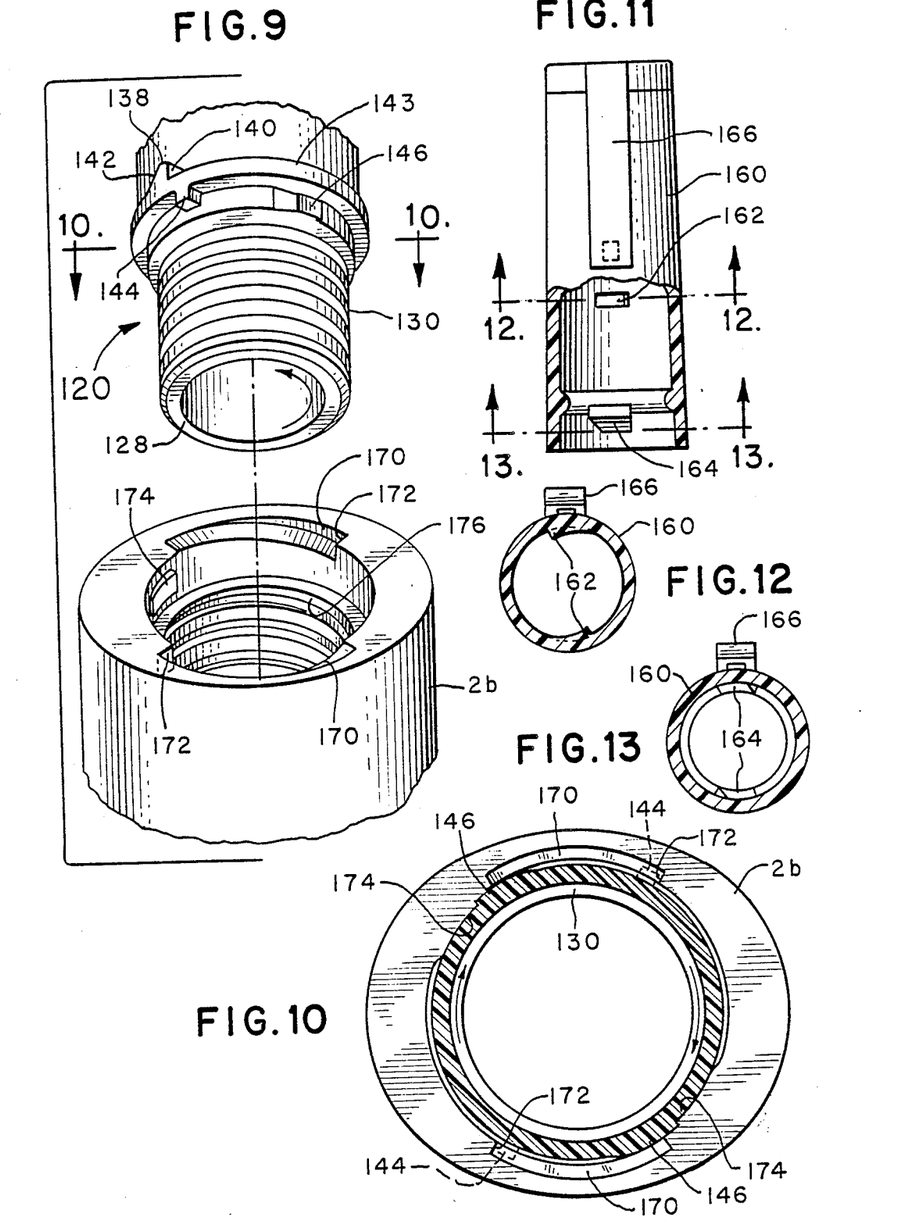
FIG. 9 is an exploded perspective view of portions of the dispensing device of FIG. 1.
FIG. 10 is a sectional view taken along line 10—10 of FIG. 9.
FIG. 11 is an elevational view in partial cutaway of the cap of FIG. 1.
FIG. 12 is a cross sectional view taken along line 12—12 of FIG. 11.
FIG. 13 is a cross sectional view taken along line 13—13 of FIG. 11.

As shown in FIGS. 2 and 9 the cartridge holder 120 mounts in the dispensing device by screwing the external threads 130 into a collar 2b defined by the dispensing device. This collar 2b defines internal threads 176 which mate with the external threads 130. In addition the collar 2b defines elements which cooperate with the stop members 144 and the ramps 146 to define the fully assembled position of the cartridge holder 120 and to hold it in that position. In particular, the collar 2b defines a pair of spiral grooves 170, each of which terminates in a transverse face 172. When the cartridge holder 120 is threaded into the collar 2b the stop members 144 enter the spiral grooves 170. The faces 172 prevent overtightening of the cartridge holder 120 in the collar 2b. The collar 2b defines ramps 174 which cooperate with the ramps 146 to define a detent that tends to hold the cartridge holder 120 in the fully assembled position (FIG. 10).

As best shown in FIG. 2, when the cartridge holder 120 is assembled in the collar 2b the rear end of the cartridge 100 is unrestrained. This arrangement provides particular advantages, because the overall length of the cartridge 100 is difficult to control with conventional manufacturing processes, as explained above. This embodiment accommodates varying lengths of the cartridge 100 because the rear rim of the cartridge body 102 does not contact the dispensing unit. In order to prevent the cartridge 100 from moving undesirably after the cartridge holder 120 has been threaded into the collar 2b, the cartridge 100 is restrained from movement by the frictional fit with the raised lands 132 described above.

As described in greater detail below, the dispensing device includes a plunger 5 that is advanced against the piston 108 to dispense the medication 110 through the needle 152.

The movement of this plunger 5 is controlled in part by a one-way mechanism that allows the plunger 5 to advance but not to retract as long as the cartridge holder 120 is mounted to the collar 2b. However, when the cartridge holder 120 is removed from the collar 2b to replace the cartridge 100, this one-way mechanism is released, to allow the plunger 5 to be retracted into the dispensing unit. The details of operation of this one-way mechanism and the manner in which this mechanism is released are explained in detail below in conjunction with FIGS. 14 and 15. Here, it is enough to note that the one-way mechanism is controlled by the axial position of a member 64 which is slidably mounted in the collar 2b. This member 64 abuts the actuating shoulder 128 of the cartridge holder 120 and is shifted rearwardly to engage the one-way mechanism with the plunger 5 when the cartridge holder 120 is mounted in place in the collar 2b.

It is the actuating shoulder 128 rather than any part of the cartridge 100 that determines the position of the one-way mechanism actuating member 64. The cartridge holder 120 can readily be manufactured to high accuracy with conventional molding techniques, and for this reason the actuating shoulder 128 can be precisely positioned to ensure that the member 64 is depressed at the proper instant, just before the cartridge holder 120 is fully assembled into the collar 2b. This ensures that there is no substantial movement of the cartridge holder 120 or the cartridge 100 after the one-way mechanism is engaged. This prevents the plunger 5 from exerting undue forces on the piston 108 and minimizes the unintended discharge of medication 110 when the needle 152 pierces the membrane 104.

Further details of the one-way mechanism, and the operation of the actuating member 64, as well as the advancing mechanism for the plunger 5 will now be described in conjunction with FIGS. 14 and 15.

Figures 14, 15:
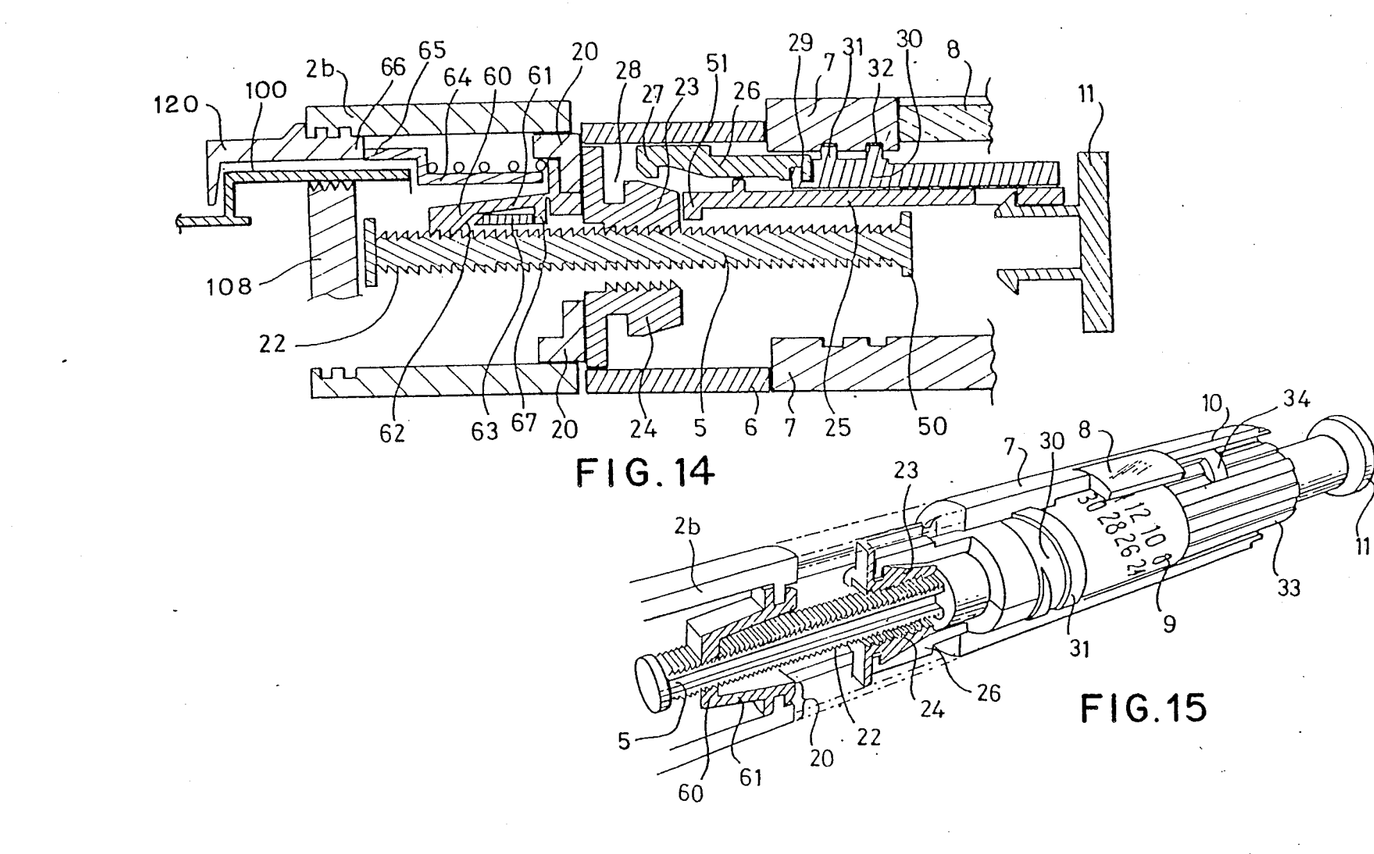
FIG. 14 is a schematic cross sectional view of portions of the dispensing device of FIG. 1.
FIG. 15 is a perspective view in partial cutaway of portions of the dispensing device of FIG. 1.

As shown in highly schematic form in FIG. 14 and as discussed above, the cartridge 100 is housed in the housing 120 which is screw fit into the collar 2b extending axially from the front end of the dispensing unit.

The dispensing device is provided with a pawl type one-way mechanism which engages teeth on the plunger 5 so as to prevent rearward movement of the plunger 5 once the housing 120 is in place. This one-way mechanism is shown at 60 in FIGS. 14 and 15 and is biassed to retract radially when the cartridge housing 120 is removed. For example, the housing can incorporate a twist mechanism which both locks the cartridge housing in position and actuates the one-way mechanism; or the shoulder 128 of the cartridge housing 120 can bear against part of the one-way mechanism as it seats home to actuate the one-way mechanism. The one-way mechanism disengages when the cartridge housing 120 is removed to allow the plunger 5 to be retracted into the device to permit a new cartridge 100 to be mounted on the dispensing device.

A preferred form of the one-way mechanism is shown in FIG. 14 and comprises a pair of diametrically opposed pawls 60 carried on spring arms 61 snap fitted onto an annular shoulder 20 to extend forward of the shoulder into the axial socket in which the cartridge 100 is received. The pawls 60 have an inclined rearward face 62 which bears against a correspondingly angled face carried by a collet 63 mounted around the plunger shank and radially inward of arms 61. The collet is attached to a spring loaded sleeve 64 which is a slideable fit within the socket and is spring biassed into its forward position. The front end of the sleeve 64 provides a stop 65 against which the shoulder 128 of the housing 120 bears as it is mounted in the device. This causes the sleeve 64 to be moved axially rearwardly to carry the inclined face of collet 63 clear of the inclined face 62 of the pawl and to bring the rear edge of collet 63 into contact with a stop 67 carried on the radially inward face of arm 61. This causes the arm 61 to flex radially inward and urge pawl 60 into engagement with the teeth on the plunger 5. When the housing 120 is removed to fit a new cartridge 100, this allows the sleeve 64 to move forward under the thrust of the spring so that collet 63 moves forward of release stop 67 and bears against the inclined face 62 to lift the pawl 60 clear of the teeth on the plunger 5. The plunger 5 can now be retracted into the device to enable another cartridge 100 to be fitted. By using the rear of the accurately molded housing 120 to actuate the pawl mechanism 60-67, rather than the rim of the cartridge 100, variations in the size of the cartridge 100 can be accommodated.

Rearwardly of shoulder 20, the body of the device houses the plunger drive mechanism, the means for engaging and disengaging the drive mechanism from the plunger, and the dosage selection means. In the form of the device shown, these take the form of a series of members concentrically journalled around the plunger 5.

As shown the housing comprises a rotatable section 6 which houses the drive engagement mechanism; a fixed section 7 containing the dosage selection mechanism and having a port 8 through which a scale 9 indicating the dose selected can be seen by the user; a further rotatable collar or sleeve 10 for operating the dosage selection mechanism: and a terminal axially operating push button 11 for driving the plunger 5 forward to dispense the selected dose. The various sections of the housing can have any desired external shape, but it is preferred that the housing 1, sleeve 6 and section 7 have an oval external cross-section so that the relative rotational position of one with respect to the other can readily be detected by a user, notably by a blind person.

The plunger 5 preferably has a substantially circular cross-section but can have a squared, triangular or other cross-section shape if desired. For example, as shown in FIG. 15, it may have two opposed flats along its length to guide the drive means.

The plunger 5 carries a series of circumferential ribs or teeth 22 which form an axial ratchet into which the one-way mechanism 21 and the radially clampable drive mechanism described below engage. The teeth 22 are of a saw tooth form with a scarp face of the teeth directed rearwardly. Preferably, the teeth extend axially for the full length of the plunger 5. It is preferred that the axial distance from one tooth to the next corresponds to a dosage unit for the material being dispensed.

Located to the rear of shoulder 20 is the drive mechanism and the mechanism for engaging and disengaging this from the plunger. The drive mechanism is a pawl type mechanism which is radially engageable and disengageable with the teeth on the plunger and comprises two jaws 23 and 24 diametrically opposed to one another and carrying on their radially inward faces teeth which correspond to and engage with the teeth 22 on the plunger.

The jaws are normally urged radially outwardly, as shown for jaw 24 in FIG. 14, by transverse coil springs acting between the jaws 23 and 24 or by other bias means (not shown) so that their teeth do not engage those of the plunger which is then free to move axially with respect to the jaws when they are in their outward position, but is locked to the jaws when they are in their radially inward position, as shown for jaw 23 in FIG. 14.

The jaws are moved radially inward against the thrust of the coil springs by a pair of cams carried on the internal face of the rotatable section 6 of the housing or formed by the narrower diameter sectors of the oval cross-section of the rotatable section 6. The user has to twist section 6 to engage or disengage the jaws from plunger 5 and thus engage or disengage the drive to the plunger. If desired, section 6 can be spring biassed towards the drive disengaging position so that the user always has to twist section 6 before the device can be used.

The shoulder 20, as shown in FIG. 14, defines the forward limit of the travel of the drive mechanism and provides the datum point from which the dosage is determined. In the device shown in FIGS. 14 and 15 the forward faces of jaws 23 and 24 butt against the rear face of shoulder 20 to set the zero or datum point for the dosage selection mechanism.

A push sleeve 25 journalled on plunger 5 and within the dosage selection mechanism described below acts axially on the rear faces of the jaws 23 and 24 when in their drive engaged position to drive the jaws and hence the plunger 5 forward. When the jaws are in the drive disengaged position, they still bear against the push sleeve so that they carry it axially rearwards with them during the dosage selection. The push sleeve 25 provides the mechanical link between the terminal push button 11 which a user presses and the jaws 23 and 24.

The jaws 23 and 24 are moved axially by means of a split jaw drive sleeve 26 which has forward hooks 27 which engage similar recesses 28 at the rear of the jaws and rearward hooks 29 or other flexible linkages which connect the sleeve 26 axially to the forward end of the screw sleeve 30 of the dosage selection mechanism. When the jaws are in the drive disengaged position as shown for jaw 24 in FIG. 14 the hooks 27 and recesses 28 are engaged and the jaws can be moved axially with the screw sleeve 30. When the jaws are in the drive engaged position, as shown for jaw 23 in FIG. 14, the hooks 27 are released from recesses 28 to permit the jaws to move axially with sleeve 25 and free from the screw sleeve 30.

The dosage selection mechanism is housed within section 7 of the housing and comprises a screw sleeve 30 journalled for rotation and axial movement upon push sleeve 25. Sleeve 30 carries an external screw thread 31 which engages a similar thread 32 carried internally by section 7 of the body of the device. Sleeve 30 is rotated and thus caused to move axially by means of a collar driving the sleeve through a spined drive 33 shown in FIG. 15. The window insert in port 8 preferably has a ratchet or clicker mechanism 34 to give an audible indication as the dose is selected.

Retraction of sleeve 30 carries the jaw drive sleeve 26 and the jaws 23 and 24 with it when they are in the disengaged position and the dose selected can be seen through port 8. Re-engagement of jaws 23 and 24 with the plunger breaks the latch 27/28 and allows the push sleeve 25 and the jaws 23 and 24 to move independently of the screw sleeve 30 and the jaw drive sleeve 26.

To indicate when there is insufficient fluid left in the cartridge to achieve the next dose, a radial shoulder or stop 50 is located at or adjacent the rearward end of plunger 5. This co-operates with a corresponding stop or shoulder 51 at the forward end of the push sleeve 25. The stops engage when the push sleeve is retracted to the maximum extent possible as the plunger 5 approaches the extreme of its forward travel. The user can then see from the dose displayed at the port 8 whether the cartridge contains the requisite amount of fluid. Since the plunger drive is not engaged at this time, the user can then set the dosage mechanism to the required dose if this is less than the amount indicated as remaining in the cartridge without having to discharge fluid as with a conventional device.

Push sleeve 25 is provided with a push button end cap 11 protruding axially from the body of the device which the user depresses to drive the sleeve 25 forward within the housing until the front face of jaws 23 and 24 butt against the rear of shoulder 20. The jaws 23 and 24 can only be moved rearwardly when they have been disengaged from the teeth 22 on the plunger 5, since the one-way mechanism will prevent rearward movement of the plunger 5. If a user attempts to set the dosage mechanism while the drive is engaged, he will detect resistance to rotation of sleeve 10. If he ignores this, the spline drive 33 between collar 10 and the screw sleeve 30 will be over-ridden to release the screw sleeve to prevent damage to the mechanism. However, unless the drive is engaged, depression of button 11 will not achieve any forward movement of the jaws or discharge of fluid from the cartridge 100.

The above device can be manufactured in many suitable materials and readily lends itself to manufacture by injection molding of suitable plastics materials with the various components being snap fits upon one another.

In operation, a user initially prepares the dispensing device for use by removing the holder 120, inserting a cartridge 100 in the holder 120, and then screwing the holder 120 into place on the collar 2b. The needle assembly 150 is then screwed into place on the housing 120. The user then rotates the sleeve 6 to disengage the drive mechanism if this has not already been done. Jaws 23 and 24 should be seated against the rear face of shoulder 20, the zero setting, from the previous use of the device, but the screw sleeve 30 will be at the dosage position previously selected. The user can thus see what dose was last administered where a sequence of different doses has to be administered. Collar 10 is rotated, say clockwise, to bring sleeve 30 to its forward position at which the latching mechanism 27/28 engages the jaws 23 and 24 and seats them firmly against the rear face of stop 20. The engagement of the latches can be used to provide an audible signal when this occurs, or the resistance to further forward movement will provide the signal to the user that the zero setting has been reached. The dosage displayed through port 8 will now read zero.

Collar 10 is then rotated counter-clockwise the desired number of turns, as evidenced by the number of clicks heard or by the dose displayed at the port 8, to retract screw sleeve 30, the jaw drive sleeve 26 and the jaws 23 and 24 and the push sleeve 25 the desired distance with respect to plunger 5. This will also cause the push button 11 to be extended from the rear end of the device. If the user inadvertently turns the collar 10 too far, it can be rotated clockwise to the correct position without moving the plunger.

Sleeve 6 is then rotated to re-engage the positive drive between the push sleeve 25, the jaws 23 and 24 and the plunger 5. This action will also disengage the latch 27/28 between jaws 23 and 24 and the jaw drive sleeve 26. At this point the device is cocked and ready to dispense the desired dose from the cartridge. However, the device has required a series of positive actions to achieve this state and would not normally be retained by a user in the cocked state, but would be stored with the drive disengaged so that accidental actuation of the device can not occur.

The user then inserts the point of needle 3 into his arm, buttock or other suitable point in his body and depresses button 11 to administer the dose of insulin. The dose is administered by depressing the button fully. If the button is not depressed fully, the user can detect this and can complete the dose administration. If desired, a colored band can be mounted around button 11 which will remain partially exposed until the button is fully depressed. Release of pressure on button 11 does not allow the plunger 5 to retract as with previous designs, so that jerky or interrupted depression of button 11 does not allow the user to pump the device to administer an excessive dose.

When the full dose has been administered, the jaws 23 and 24 will butt against the rear of shoulder 20. Due to the action of the one-way mechanism 21. 60–67, the blocks 23 and 24 cannot be retracted and administration of a further dose of insulin is not possible until the whole process of dose selection and re-cocking of the device is carried out. The device will therefore resist accidental overdosing due to repeated pressing of button 11.

As stated above, the cartridge-holder assembly of this invention finds use wherever it is desired to provide a removable cartridge for a measured dose syringe, for example in the administration of other medicaments or in dispensing accurately known amounts of a fluid, for example in blood tests or analytical work. It will also be appreciated that the assembly may be altered in ways which do not affect the fundamental operating concept of the assembly, for example by using other materials and configurations.

It is therefore intended that the foregoing detailed description be regarded as illustrative rather than limiting, and that it be understood that it is the following claims, including all equivalents, which are intended to define the scope of this invention.

I claim:

1. A cartridge assembly for a syringe-type medication dispensing unit, said assembly comprising:
   a cartridge comprising a cartridge body having first and second ends, a pierceable membrane mounted at the first end, and a piston mounted at the second end, with a volume of mediation contained in the cartridge body between the membrane and the piston;
   a cartridge holder having first and second ends, said first holder end defining a central opening and means for mounting a double ended needle, said second holder end defining means for securing the holder to a medication dispensing unit and an actuating shoulder, said holder defining a central cavity;

one of said central cavity and said cartridge being shaped with a plurality of raised lands adapted to frictionally to engage the opposed surface of the other of said cartridge and cavity so as to form an assembly which can be handled as a single modular unit with the cartridge held securely in the holder.

2. The invention of claim 1 wherein the double ended needle mounting means comprises a first set of external threads.

3. The invention of claim 1 wherein the holder securing means comprises a second set of external threads.

4. A cartridge assembly for a syringe-type medication dispensing unit, said assembly comprising:
   a cartridge comprising a cartridge body having first and second ends, a pierceable membrane mounted at the first end, and a piston mounted at the second end, with a volume of medication contained in the cartridge body between the membrane and the piston;
   a cartridge holder having first and second ends, said first holder end defining a central opening and means for mounting a double ended needle, said second holder end defining means for securing the holder to a medication dispensing unit and an actuating shoulder, said holder defining a central cavity shaped to receive and frictionally engage the cartridge to form an assembly which can be handled as a single, modular unit with the cartridge held securely in the holder;
   wherein the holder securing means comprises a second set of external threads; and
   wherein the modular unit is mounted to a syringe type medication dispensing unit having a plunger engageable with the piston, a one-way mechanism engaged with the plunger, and an actuating member for the one-way mechanism, wherein the second holder end is received within the dispensing unit, wherein the second set of external threads is engaged with the dispensing unit, and wherein the actuating shoulder is engaged with the actuating member.

5. The invention of claim 4 wherein the dispensing unit and the holder define a detent system which holds the second set of external threads in engagement with the dispensing unit.

6. The invention of claim 5 wherein the detent system comprises inter engaging ramps on the holder and the dispensing device adjacent the second set of external threads.

7. The invention of claim 1 wherein the modular unit is mounted to a cap which encloses the first end of the holder, wherein the holder defines at least one stop member wherein the cap defines at least one lug, wherein at least one of the stop member and lug has a transverse face and a sloping face oriented such that the stop member and lug abut at the transverse face to limit rotation of the cap when the cap is rotated in a first direction with respect to the holder, and the stop member and the lug abut at the sloping face to shift the cap axially along the holder when the cap is rotated in a second direction with respect to the holder.

8. The invention of claim 1 wherein the modular unit is mounted to a cap which encloses the first end of the holder; wherein one of the holder and the cap defines at least one groove having an axial portion and a circumferential portion; and wherein the other of the holder and the cap defines a protruding element shaped to slide in the groove to secure the cap and holder together in a bayonet mount.

9. The invention of claim 1 wherein the holder frictionally engages only the first end of the cartridge.

10. The invention of claim 9 wherein the cartridge defines an annular collar disposed around the membrane, and wherein the holder frictionally engages the cartridge only at the collar.

11. The invention of claim 10 wherein the plurality of raised lands are positioned on the holder to frictionally engage the collar.

12. The invention of claim 2 further comprising:
    a needle assembly comprising a double ended needle secured to a mounting element which defines a set of internal threads engaged with the first set of external threads of the holder, with one end of the needle passing through the membrane and in contact with the medication.

13. The invention of claim 1 wherein the medication comprises an insulin solution.

14. The invention of claim 1 wherein the second end of the cartridge extends out of the holder by a distance of about ½ inch or more.

15. A cartridge assembly for a syringe-type medication dispensing unit, said assembly comprising:
    a cartridge comprising a cartridge body having first and second ends, a pierceable membrane mounted at the first end, and a piston mounted at the second end, with a volume of medication contained in the cartridge body between the membrane and the piston and an annular collar disposed around the membrane;
    a cartridge holder having first and second ends, said first holder end defining a central opening and a first set of external threads, said second holder end defining an actuating shoulder and a second set of external threads said holder defining a central cavity shaped to receive the cartridge with the pierceable membrane adjacent the central opening, said cartridge having a length greater than that of the holder such that the second end of the cartridge extends out of the holder,
    said holder defining a plurality of raised lands positioned to frictionally engage the collar to form an assembly which can be handled as a single, modular unit with the cartridge held removably in the holder by friction between the collar and the holder, said holder shaped to receive the cartridge freely until the lands engage the collar, such that the weight of the cartridge will move the cartridge into the holder until the lands contact the collar.

16. The invention of claim 15 wherein the modular unit is mounted to a syringe type medication dispensing unit having a plunger engageable with the piston, a one-way mechanism engaged with the plunger, and a one-way mechanism actuating member, wherein the second hold end is received within the dispensing unit, wherein the second set of external threads is engaged with the dispensing unit, and wherein the actuating shoulder is engaged with the one-way mechanism actuating member.

17. The invention of claim 16 wherein the dispensing unit and the holder define a detent system which the second set of external threads in engagement with the dispensing unit.

18. The invention of claim 17 wherein the detent system comprises inter-engaging ramps on the holder and the dispensing device adjacent the second set of external threads.

19. The invention of claim 18 wherein the modular unit is mounted to a cap which encloses the first end of the holder, wherein the holder defines at least one stop member, wherein the cap defines at least one lug, wherein at least one of the stop member and lug has a transverse face and a sloping face oriented such that the stop member and lug abut at the transverse face to limit rotation of the cap when the cap is rotated in a first direction with respect to the holder, and the stop member and the lug abut at the sloping face to shift the cap axially along the holder when the cap is rotated in a second direction with respect to the holder.

20. The invention of claim 15 wherein the modular unit is mounted to a cap which encloses the first end of the holder; wherein one of the holder and the cap defines at least one groove having an axial portion and a circumferential portion; and wherein the other of the holder and the cap defines a protruding element shaped to slide in the groove to secure the cap and holder together in a bayonet mount.

21. The invention of claim 15 further comprising:
a needle assembly comprising a double ended needle secured to amounting element which defines a set of internal threads engaged with the first set of external threades of the holder, with one end of the needle passing through the membrane and in contact with the medication.

22. The invention of claim 15 wherein the medication comprises insulin.

23. The invention of claim 15 wherein the lands are axially oriented.

* * * * *

UNITED STATES PATENT AND TRADEMARK OFFICE
CERTIFICATE OF CORRECTION

PATENT NO. : 4,936,833

DATED : June 26, 1990

INVENTOR(S) : Bernard Sams

It is certified that error appears in the above-identified patent and that said Letters Patent is hereby corrected as shown below:

IN THE CLAIMS

Col. 10, line 59, claim 1, delete "mediation" and substitute therefor --medication--;

Col. 12, line 58, claim 16, delete "hold" and substitute therefor --holder--.

Col. 12, line 64, claim 17, after "which" insert --holds--.

Col. 14, line 8, claim 21, delete "amounting" and substitute therefor --a mounting--.

Col. 14, line 10, claim 21, delete "threades" and substitute therefor --threads--.

Signed and Sealed this

Twenty-second Day of December, 1992

Attest:

DOUGLAS B. COMER

*Attesting Officer*   *Acting Commissioner of Patents and Trademarks*